(12) United States Patent
Guder et al.

(10) Patent No.: US 12,376,793 B2
(45) Date of Patent: Aug. 5, 2025

(54) COMPONENT

(71) Applicant: IMPERIAL COLLEGE OF SCIENCE, TECHNOLOGY AND MEDICINE, South Kensington London (GB)

(72) Inventors: Firat Guder, London (GB); Yasin Cotur, London (GB); Michael Kasimatis, London (GB)

(73) Assignee: IMPERIAL COLLEGE OF SCIENCE, TECHNOLOGY AND MEDICINE, London (GB)

( * ) Notice: Subject to any disclaimer, the term of this patent is extended or adjusted under 35 U.S.C. 154(b) by 1127 days.

(21) Appl. No.: 17/266,947

(22) PCT Filed: Aug. 6, 2019

(86) PCT No.: PCT/EP2019/071157
§ 371 (c)(1),
(2) Date: Feb. 8, 2021

(87) PCT Pub. No.: WO2020/030660
PCT Pub. Date: Feb. 13, 2020

(65) Prior Publication Data
US 2021/0298671 A1    Sep. 30, 2021

(30) Foreign Application Priority Data

Aug. 6, 2018   (GR) ............................ 20180100367
Aug. 21, 2018  (GB) .................................... 1813568

(51) Int. Cl.
*H04R 1/46* (2006.01)
*A61B 5/00* (2006.01)
*A61B 7/04* (2006.01)

(52) U.S. Cl.
CPC ............... *A61B 5/683* (2013.01); *A61B 7/04* (2013.01); *A61B 5/6831* (2013.01);
(Continued)

(58) Field of Classification Search
CPC ..... A61B 7/00; A61B 7/04; A61B 2562/0204; H04R 1/46
See application file for complete search history.

(56) References Cited

U.S. PATENT DOCUMENTS 4,473,080 A    9/1984  Paavola
4,483,343 A *  11/1984 Beyer .................... G10K 11/02
                                                73/644

(Continued)

FOREIGN PATENT DOCUMENTS

CN      207341767     5/2018
WO   WO 2017/015286 A1  1/2017

OTHER PUBLICATIONS

PCT ISR and Written Opinion of the ISA for PCT/EP2019/071157, dated Nov. 15, 2019, 15 pages.

(Continued)

*Primary Examiner* — Ryan Robinson
(74) *Attorney, Agent, or Firm* — Husch Blackwell

(57) ABSTRACT

A component for use in a transducer arrangement includes a flexible membrane that defines a contact surface. An enclosed volume is also defined at least partially by the flexible membrane, and a is liquid contained within the enclosed volume.

22 Claims, 10 Drawing Sheets

(52) U.S. Cl.
CPC ....... *A61B 2503/40* (2013.01); *A61B 2562/12* (2013.01); *A61B 2562/164* (2013.01); *A61B 2562/168* (2013.01)

(56) References Cited

U.S. PATENT DOCUMENTS

| | | | | |
|---|---|---|---|---|
| 4,672,976 A * | 6/1987 | Kroll | ........................ | A61B 7/04 381/364 |
| 4,947,859 A * | 8/1990 | Brewer | .................... | A61B 7/04 381/364 |
| 4,995,401 A * | 2/1991 | Bunegin | ................ | A61B 5/031 600/595 |
| 5,022,402 A * | 6/1991 | Schieberl | ............. | A61B 5/0002 600/528 |
| 5,817,035 A * | 10/1998 | Sullivan | ............. | A61B 5/02411 600/588 |
| 5,853,005 A * | 12/1998 | Scanlon | ............... | A61B 5/6896 381/166 |
| 6,438,238 B1 * | 8/2002 | Callahan | .............. | A61B 5/6843 D24/134 |
| 6,468,238 B1 | 10/2002 | Hawkins et al. | | |
| 7,489,967 B2 * | 2/2009 | Von Arx | .............. | A61B 5/0031 607/32 |
| 7,615,012 B2 * | 11/2009 | Von Arx | ................. | A61B 7/023 600/528 |
| 11,672,423 B2 * | 6/2023 | Kim | ........................ | G01H 11/06 600/552 |
| 2003/0199771 A1 * | 10/2003 | Baruch | ................ | A61B 5/0285 600/485 |
| 2003/0212346 A1 | 11/2003 | Lambert | | |
| 2006/0047215 A1 | 3/2006 | Newman et al. | | |
| 2012/0232427 A1 * | 9/2012 | Bakema | .................... | B06B 1/06 600/586 |

OTHER PUBLICATIONS

GB Combined Search and Examination Report for GB1813568.1, dated Feb. 14, 2019, 9 pages.

* cited by examiner

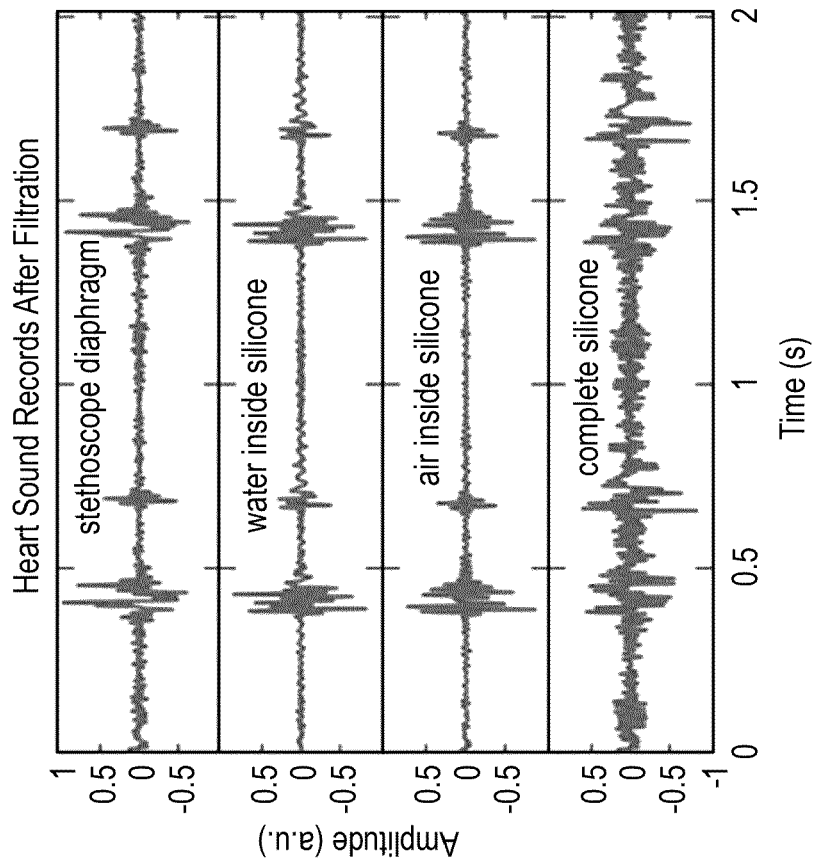
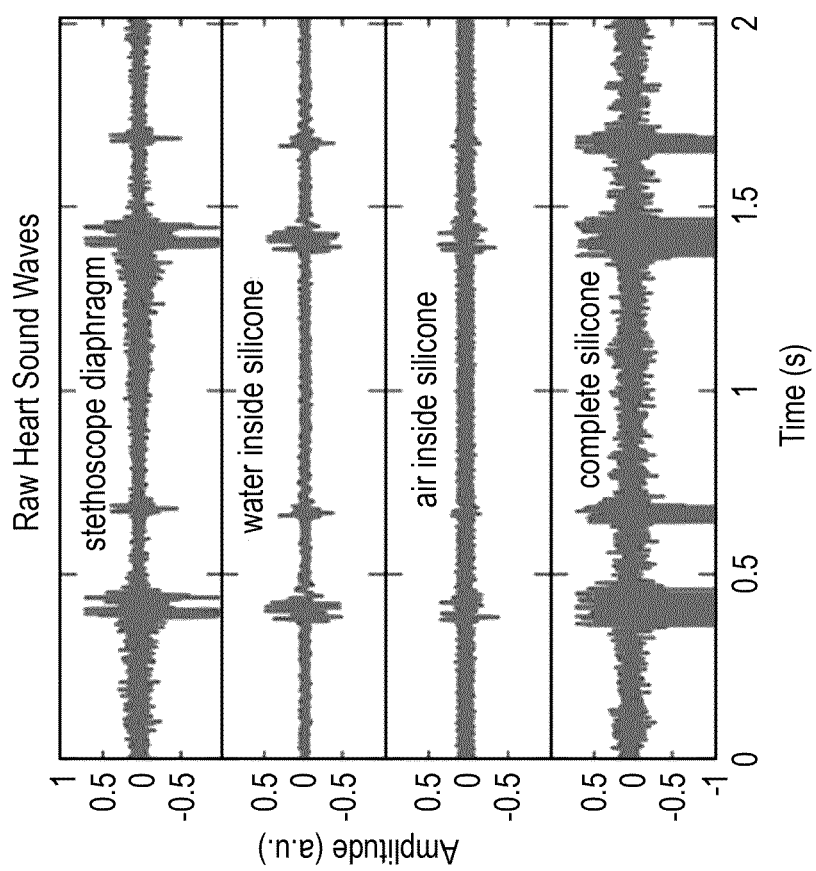
Fig. 7B
Fig. 7A

| Material | D1(mm) | Ecoflex raw data | Ecoflex filtered | D-Skin raw data | D-Skin filtered |
|---|---|---|---|---|---|
| Water inside silicone device | 15 | 0.38 | 0.14 | 0.88 | 0.20 |
| | 30 | 0.28 | 0.08 | 0.57 | 0.20 |
| | 60 | 0.40 | 0.19 | 0.36 | 0.22 |
| Air inside silicone device | 15 | 0.58 | 0.13 | 1.00 | 0.22 |
| | 30 | 0.61 | 0.09 | 0.67 | 0.33 |
| | 60 | 0.86 | 0.14 | 0.45 | 0.26 |
| Complete silicone device | 15 | 1.00 | 0.49 | 0.54 | 0.23 |
| | 30 | 0.59 | 0.12 | 0.47 | 0.15 |
| | 60 | 0.28 | 0.20 | 0.52 | 0.17 |

| Stethoscope | | 0.89 | 0.27 | | |
|---|---|---|---|---|---|

Fig. 9

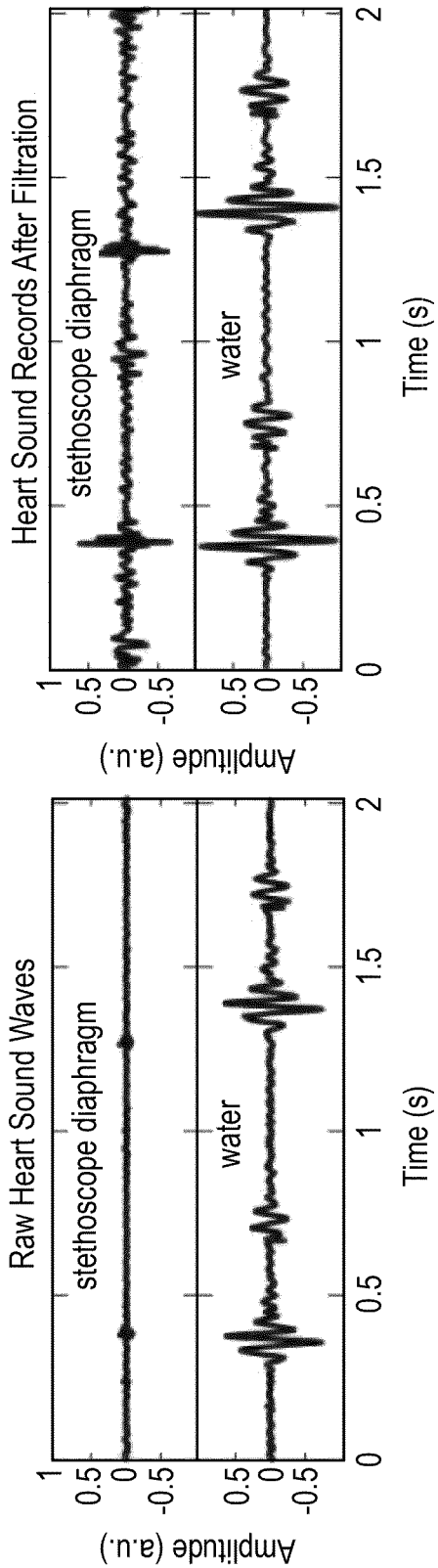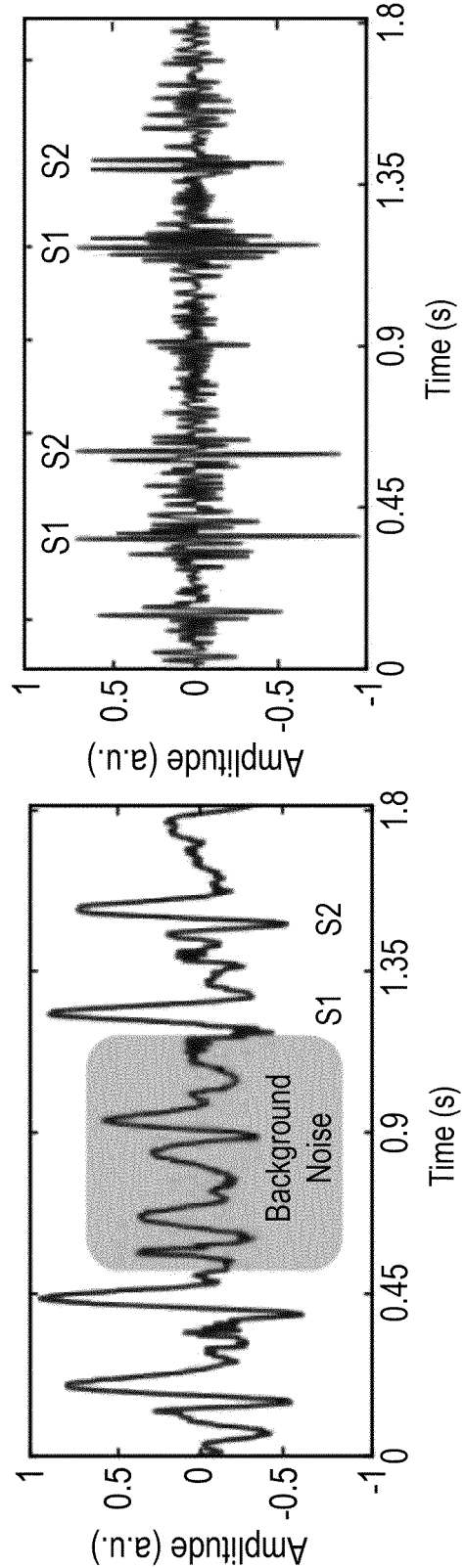

COMPONENT

RELATED APPLICATIONS

The present application is a National Phase entry of PCT Application No. PCT/EP2019/071157, filed Aug. 6, 2019, which claims priority from GR Application No. 20180100367, filed Aug. 6, 2018, and Great Britain Application No. 1813568.1, filed Aug. 21, 2018, all of these disclosures being hereby incorporated by reference in their entirety.

FIELD

The present disclosure relates to a component for use in a transducer arrangement, a transducer arrangement, and a wearable transducer system. The disclosure also relates to a method for measuring vital signs in humans or animals. A method for manufacturing a component is also disclosed.

BACKGROUND

In modern global healthcare systems, wearable devices have taken a central role in the remote monitoring of vital signs of the human or animal body. Vital signs include, for example, heart rate, panting rate, and gut sounds. Wearable devices can provide for unobtrusive and continuous monitoring of vital signs of a body without sacrificing user comfort. However, the measuring of vital signs using current wearable devices can be challenging due to body movement, hairy skin, clothing, and poor signal quality.

For example, photoplethysmography (PPG) sensors for measuring heart rate require hair free skin and usually a compensation of motion artefacts. Electrocardiography (ECG) sensors for measuring cardiac cycles require conductive gels to provide sufficient adhesion to the skin. Remote measurement methods such as ballistocardiography (BCG) and seismocardiography (SCG) fail on moving bodies due to motion artefacts.

Further examples include polymer based pressure sensors for long-term domestic heart rate monitoring. Such devices require direct contact with the skin, fail when the tissue is wet, and may also cause irritation or allergic reactions.

Another example is phonocardiography (PCG), which is a method for detecting heart sounds. There are two major heart sounds: the lub sound (S1) which arises during the closure of mitral and tricuspid valves in the beginning of the systole, and the dub sound (S2) which occurs during the closure of aortic and pulmonic valves. In PCG, movement of the microphone causes a rustling noise which results in improper readings.

In addition to the area of measuring vital signs from the human or animal body, movement and outside noise can also prove challenging in the area of measuring sound from musical instruments, for example by using devices such as pickups.

The present disclosure seeks to alleviate, at least to a certain degree, the problems and/or to address at least to a certain extent, the difficulties associated with the prior art.

SUMMARY

According to a first aspect of the disclosure, there is provided a component for use in a transducer arrangement, comprising: a flexible membrane comprising a contact surface, an enclosed volume defined at least partially by said flexible membrane, and a liquid contained within said enclosed volume.

Advantageously, the component can be used to establish good contact even with hairy or clothed regions of skin and good signal quality, and thus can enable to monitoring of vital signs without shaving the body or the removal of clothing.

Optionally, the flexible membrane may comprise an elastomer. Advantageously, this provides flexibility and stretchability to the component such that the component is flexible and elastic enough to conform to the surface contours of a subject such as the body of a human or animal, but also sufficiently stiff to generally maintain its shape. Advantageously, this can provide for the reduction of noise of a signal obtained by a transducer arrangement including the component.

Optionally, the enclosed volume may be defined fully by an elastomer. Advantageously, this provides flexibility and stretchability to the component, such that the component is flexible and elastic enough to conform to the surface contours of a subject such as the body of a human or animal, but also sufficiently resilient to generally maintain its shape. Advantageously, this can provide for the reduction of noise of a signal obtained by a transducer arrangement including the component.

Optionally, the elastomer may comprise one or more of silicone, acrylic, nitrile and polyurethane.

Optionally, the elastomer may comprise platinum-catalysed silicone.

Optionally, at least a part of a boundary enclosing the enclosed volume may have a material thickness of between approximately 0.05 mm to approximately 5 mm, or between approximately 1.5 mm to approximately 2.5 mm, or approximately 2 mm, or approximately equal to or less than 2 mm. Advantageously, when used in a transducer arrangement, this can provide for improved measuring of a signal by a transducer arrangement including the component, by balancing the effects of increasing flexibility of the component with increasing material thickness and decreasing component shape stiffness with decreasing material thickness, to establish good conformity and contact with a subject.

Optionally, the contact surface may be substantially planar. Advantageously, this ensures good conformity and contact with a subject.

Optionally, the contact surface may be generally circular or elliptical in shape. Advantageously, this provides for good conformity with a subject by providing a generally circular footprint when the contact surface is not stretched or stretched respectively, when contacting a subject.

Optionally, the component may further comprise a surface configured to receive a transducer.

Optionally, the contact surface and the surface configured to receive a transducer may be substantially parallel.

Optionally, the maximum internal spacing in a direction substantially perpendicular to the contact surface between the contact surface and the surface configured to receive a transducer may define a first depth of the liquid. The first depth of the liquid may be between approximately 5 mm to approximately 70 mm, or between approximately 15 mm to approximately 60 mm, or between approximately 10 mm to approximately 20 mm, or approximately 15 mm, or approximately 30 mm, or approximately 60 mm. Advantageously, this provides for improved measuring of a signal by balancing the effects of increasing signal attenuation and reduced noise as the first depth increases, for a signal measured using a transducer arrangement including the component. The internal spacing between the contact surface and the surface for the transducer may be determined depending on the type of transducer being used, the application of the device, and the stiffness of the materials of the boundary defining the enclosed volume and the liquid contained within the enclosed volume.

Optionally, the contact surface may comprise a first outer surface and a first inner surface, and the surface configured to receive a transducer may comprise a second outer surface and a second inner surface.

Optionally, the maximum internal spacing in a direction substantially perpendicular to the contact surface between the contact surface and the surface configured to receive a transducer may be defined as the maximum internal spacing in a direction substantially perpendicular to the contact surface between the first inner surface and the second inner surface.

Optionally, the surface configured to receive a transducer may comprise a recess for receiving said transducer. Advantageously, this provides for the component to be used in a transducer arrangement.

Optionally, the internal spacing in a direction substantially perpendicular to the contact surface between the contact surface and the surface configured to receive a transducer in the region of the recess may define a second depth of the liquid. The second depth of the liquid may be between approximately 1 mm to approximately 10 mm less than the first depth, or approximately 5 mm less than the first depth.

Optionally, the internal spacing in a direction substantially perpendicular to the contact surface between the contact surface and the surface configured to receive a transducer in the region of the recess may be defined as the internal spacing in a direction substantially perpendicular to the contact surface between the first inner surface and the second inner surface in the region of the recess. Optionally, the component may further comprise one or more surfaces extending between the contact surface and the surface configured to receive a transducer, such that the enclosed volume is defined fully therebetween.

Optionally, one of the contact surface and the surface configured to receive a transducer can be larger in size than the other of the contact surface and the surface configured to receive a transducer.

Optionally, the contact surface is larger in size than the surface configured to receive a transducer.

Optionally, the enclosed volume may generally have the shape of a truncated cone. Advantageously, this provides for the component to be sufficiently flexible but stiff or resilient to maintain its shape but ensure good conformity and contact with the surface of a subject such as a contoured surface of the body of a human or animal.

Optionally, the liquid may have a density substantially similar to the density of human or animal body tissue. Advantageously, and surprisingly, when used in a transducer arrangement for measuring vital signs in the body of a human or animal, the liquid can then provide for sounds waves to travel through the body to the liquid with minimal disruption to wave propagation, to provide for a less noisy signal.

Optionally, the liquid may comprise one or more of water and oil and a gel. Advantageously, this provides for a flexible and elastic component with stable properties and performance over time.

Optionally, the liquid may comprise distilled water. Advantageously, this reduces or avoids the inclusion of impurities and/or minerals in the liquid to reduce or avoid the build-up of mineral deposits or other deposits in the enclosed volume of the component to ensure for stable properties and performance of the component over time and to maintain the flexibility and stretchability of the component.

Optionally, the liquid may completely fill the enclosed volume. Advantageously, this reduces or avoids the formation or inclusion of air bubbles or other fluids in the enclosed volume to ensure for stable properties and performance over time and to maintain the flexibility and stretchability of the component.

According to a second aspect of the disclosure, there is provided a transducer arrangement comprising the component in accordance with the first aspect and/or any optional feature thereof, and a transducer.

Optionally, the transducer may be a sensor. Advantageously, this provides for the transducer arrangement to be used to measure a physical quantity.

Optionally, the transducer may be configured to measure sound. Advantageously, this provides for the transducer arrangement to be used to measure audio vital signs such as heart sounds.

Optionally, the transducer may be a microphone.

Optionally, the transducer may be an electret microphone.

Optionally, the transducer may be a MEMS microphone.

Optionally, the transducer may be an accelerometer.

Optionally, the transducer may be encapsulated with a flexible material. Advantageously, this provides flexibility and stretchability to the transducer arrangement.

According to a third aspect of the disclosure, there is provided a wearable transducer system comprising the transducer arrangement according to the second aspect and/or any optional feature thereof and an attachment element for attaching said transducer arrangement to a human or animal. Advantageously, this provides for the transducer arrangement to be securely and stably attached to the body of a human or animal to provide for the continuous monitoring of vital signs.

Optionally, the attachment element may comprise a strap member. Advantageously, this provides for the transducer arrangement to be attached to a human or animal in a secure and stable manner.

Optionally, the attachment element may comprise an elastomer. Advantageously, this provides for a flexible and stretchable attachment element.

Optionally, the attachment element may comprise silicone. Advantageously, this provides for a flexible and stretchable attachment element which is soft, conformable, chemically safe, hydrophobic, biocompatible, stable, and resistant to degradation.

Optionally, the attachment element may comprise a housing volume for receiving a device.

Optionally, the device comprises a printed circuit board and/or a power source.

Optionally, the housing volume is generally cuboidal.

According to a fourth aspect of the disclosure, there is provided a method of measuring vital signs in humans or animals using the component of the first aspect and/or any optional feature thereof, or the transducer arrangement of the second aspect and/or any optional feature thereof, or the wearable transducer system of the third aspect and/or any optional feature thereof.

According to a fifth aspect of the disclosure, there is provided a method for manufacturing a component, comprising: providing a mould arrangement defining a shape which defines a partially enclosed volume, pouring or introducing a first portion of pre-polymer elastomer into said mould arrangement, at least partially curing said first portion of pre-polymer elastomer to form a first elastomer portion which defines a partially enclosed volume, pouring or introducing a liquid into the partially enclosed volume defined by said first elastomer portion to fully fill said partially enclosed volume, pouring or introducing a second portion of pre-polymer elastomer on top of said liquid, and at least partially curing said second portion of pre-polymer elastomer to form a substantially planar second elastomer portion on top of said liquid. Optionally, the component may be for use in a transducer arrangement, such as a component according to the first aspect.

Optionally, one or more of the first portion of pre-polymer elastomer and the second portion of pre-polymer elastomer may comprise liquid silicone, such that one or more of the first elastomer portion and the second elastomer portion comprises silicone. Optionally, both the first and second portions of pre-polymer elastomer may comprise liquid silicone, such that both the first and second elastomer portions comprise silicone. Optionally, the liquid may be water. Optionally, the first and second pre-polymer elastomer portions and the liquid may be any other materials which provide that the liquid maintains the second portion of pre-polymer elastomer on top of said liquid through surface tension or density and does not prevent the curing, polymerisation and/or cross-linking of the second portion of pre-polymer elastomer to form the second elastomer portion. Advantageously, the second portion of pre-polymer elastomer will not mix with the liquid or sink. Advantageously, this prevents the formation of air bubbles in the enclosed volume and the second portion of pre-polymer elastomer will stick to and cure together with the at least partially cured first portion of pre-polymer elastomer.

Optionally, the mould arrangement may be fabricated using an additive manufacturing process such as 3D printing.

Optionally, the mould arrangement may define a shape which defines at least partially the enclosed volume.

Optionally, the mould arrangement may have a first portion and a second portion.

Optionally, the method further includes providing a recess in one of said first or second silicone portions and mounting a transducer in said recess.

BRIEF DESCRIPTION OF THE DRAWINGS

The present disclosure may be carried out in various ways and examples of the disclosure will now be described by way of example to the accompanying drawings, in which:

FIG. 7A shows raw heart sound signals collected using four different devices, including a transducer arrangement;

FIG. 7B shows the heart sound signals of FIG. 7A filtered;

FIG. 9 shows a comparison of the performance of components made with different dimensions and from different materials in the form of dynamic time warping (DTW) data;

FIG. 10A shows raw heart sound signals collected using a transducer arrangement and a known stethoscope diaphragm;

FIG. 10B shows the heart sound signals of FIG. 10A filtered;

FIG. 11A shows a heart sound signal of a dog collected using a transducer arrangement;

FIG. 11B shows the heart sound signal of FIG. 11A filtered;

DETAILED DESCRIPTION

Figure 1:
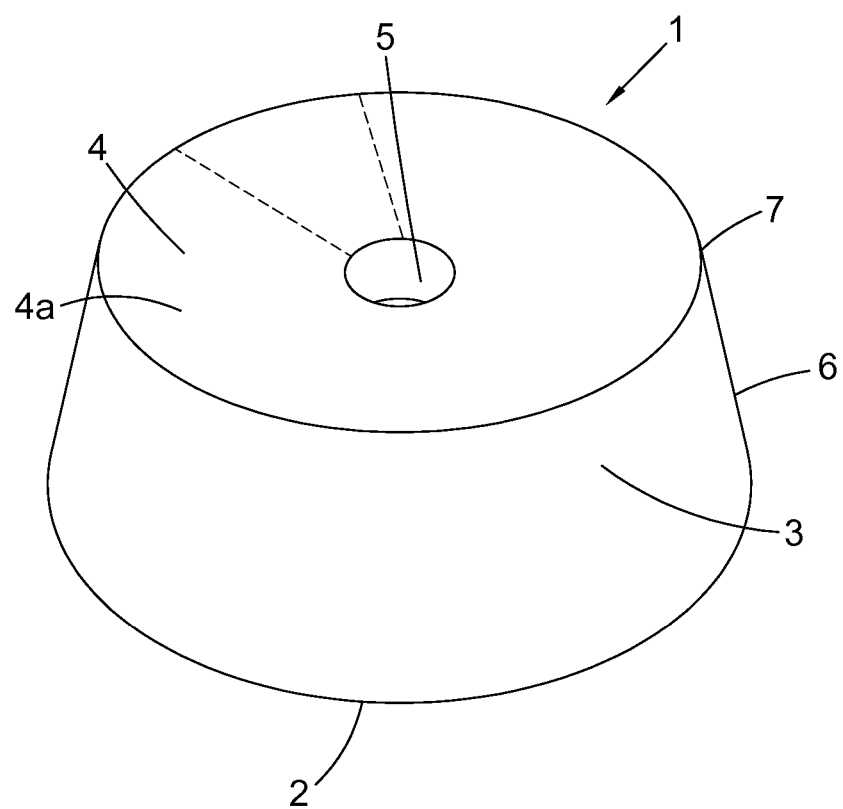
FIG. 1 illustrates a component for use in a transducer arrangement.
Figure 2:
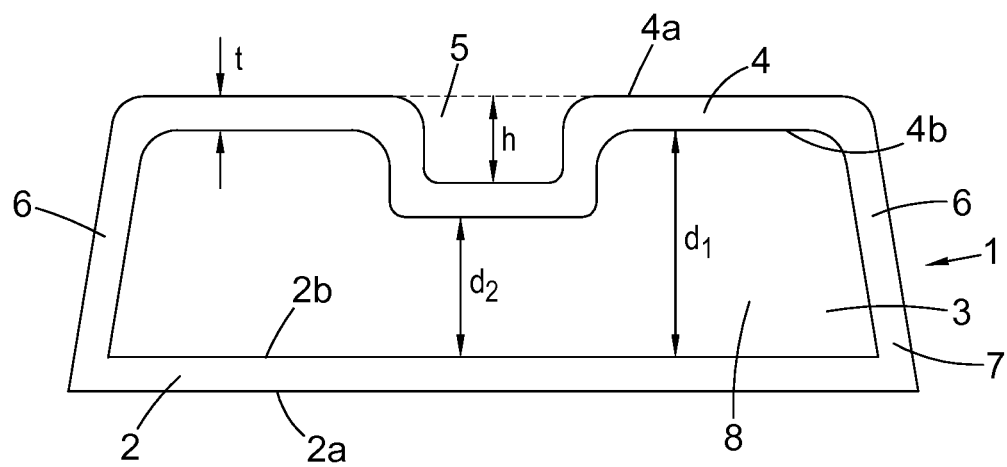
FIG. 2 illustrates a cross-sectional view of the component of FIG. 1.

FIG. 1 illustrates a component 1 for use in a transducer arrangement. FIG. 2 shows a cross-sectional view of the component 1 of FIG. 1. The component comprises a flexible membrane comprising a contact surface 2. The contact surface 2 is configured to contact a surface of a subject, such as a human, an animal, a musical instrument, or a surface of any other subject from which a physical quantity can be measured. An enclosed volume 3 is defined at least partially by the flexible membrane. A liquid 8 is contained within the enclosed volume 3.

The boundary 7 enclosing the enclosed volume 3 has a generally constant material thickness of approximately 2 mm. Advantageously, when used in a transducer arrangement, this can provide for improved measuring of a signal by a transducer arrangement including the component 1, by balancing the effects of increasing flexibility of the component 1 with increasing material thickness and decreasing component shape stiffness with decreasing material thickness, to establish good conformity and contact with a subject. The contact surface 2 is substantially planar. This is to ensure optimum contact with a subject. The contact surface 2 is of a generally isotropic shape, so that if the design of a strap 12 (shown in FIGS. 4 to 6) which can be used to attach the component 1 to a human or animal were to change, fewer considerations would have to be made to alter the component's shape. In the example, the generally isotropic shape is a circle. This shape of contact surface is advantageous because it provides for good conformity with a subject, such as the body of a human or animal, or a surface or a musical instrument.

Alternatively, the contact surface 2 can be generally elliptical in shape. An elliptically shaped contact surface is advantageous because if, for example, a component 1 with a circular contact surface is attached to the body of a human or animal by means of a strap 12, if the strap 12 is stretched to cover the body firmly, the contact surface will be stretched, thus stretching the circular contact surface into an elliptical shape. If the contact surface is generally elliptical in shape, then the contact surface can be stretched in a direction perpendicular to the direction of stretching when applied to the body, in order to compensate for said stretching and stretch the contact surface into a circular shape. This means that once stretched and firmly fitted to a subject such as the body of a human or animal, using a strap 12 for example, the contact surface would have a circular footprint.

A circular footprint is advantageous to provide for good conformity and surface contact with a subject.

Figure 3:
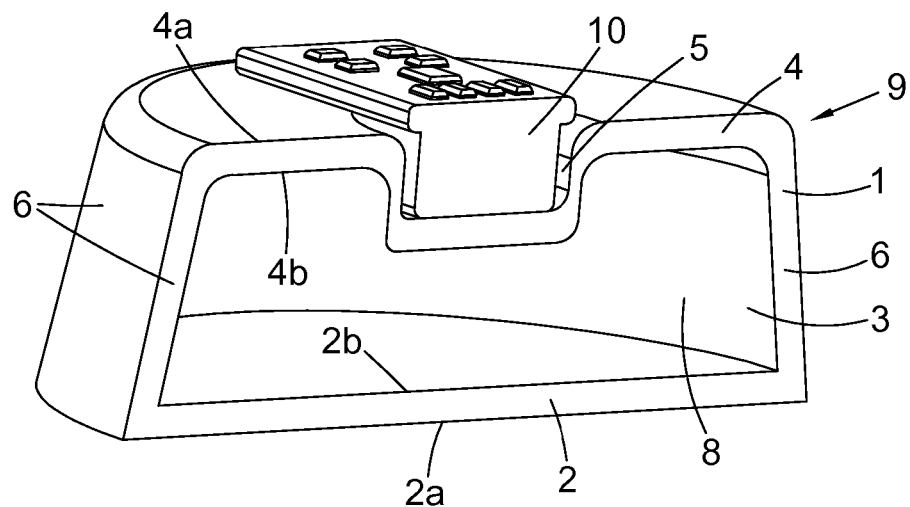
FIG. 3 illustrates a cross-sectional view of a transducer arrangement.

As shown in FIG. 2, the component 1 includes an upper surface 4, which is a surface configured to receive a transducer. The transducer surface 4 and the contact surface 2 are substantially parallel. The transducer surface 4 has a recess 5 which is configured or shaped for receiving a transducer 10. As shown in FIG. 3, a transducer 10, such as an electret microphone, is mounted or attached to and/or housed within the recess 5. Though, other means can be employed to mount or attach the transducer 10 to the transducer surface 4. The recess 5 is positioned approximately in the centre of the transducer surface 4. In the example shown in FIG. 1, the transducer surface 4 is generally circular, and the recess 5 is generally circular and positioned approximately in the centre of the transducer surface 4. Though, it is envisaged that like the contact surface 2, the transducer surface 4 can also be elliptical.

As shown in FIG. 2, the lower, contact surface 2 has an outer surface 2a and an inner surface 2b. The transducer surface 4 has an outer surface 4a and an inner surface 4b. The inner surfaces 2b and 4b at least partially define the enclosed volume 3. Since the contact surface 2 is substantially planar, i.e. substantially flat, and the contact surface and the transducer surface 4 are substantially parallel, there is defined by the contact surface 2 and the transducer surface 4 a first depth d1 adjacent to the area of the recess 5 for the transducer, and a second depth d2 is the region of the recess 5, of the enclosed volume 3 and of the liquid 8. As shown in FIG. 2, the maximum internal spacing in a direction substantially perpendicular to the contact surface 2 between the contact surface 2 and the transducer surface 4 is defined by the maximum internal spacing in a direction substantially perpendicular to the contact surface 2 between the inner surfaces 2b and 4b. Said maximum internal spacing defines a first depth d1 of the enclosed volume 3 and of the liquid 8. The value of the first depth d1 can be chosen to balance the effects of increasing signal attenuation and reduced noise as d1 increases. D1 should be large enough such that when the component 1 is stretched in a direction substantially parallel to the contact surface 2 and/or the transducer surface 4, for example when placed on a surface of a subject, the contact surface 2 and the transducer surface 4 do not come into contact. This can be determined by taking into account the stiffness of the materials of the boundary defining the enclosed volume and also the liquid within the enclosed volume. In the example, d1 is 15 mm. The optimisation of d1 shall be detailed in the succeeding paragraphs. Though, depending on the size and application of a particular component, d1 can be more or less than 15 mm.

The internal spacing in a direction substantially perpendicular to the contact surface 2 between the contact surface 2 and the transducer surface 4 in the region of the recess 5 is defined by the internal spacing in a direction substantially perpendicular to the contact surface 2 between the inner surfaces 2b and 4b in the region of the recess 5. Said internal spacing defines a second depth d2 of the enclosed volume 3 and of the liquid 8. In the example, the second depth d2 of the liquid 8 is approximately 5 mm less than the first depth d1 to provide a depth to receive a transducer. As shown in FIG. 2, the difference between the first depth d1 and the second depth d2 is defined by the depth h of the recess 5. The shape, size and position of the recess 5 can be varied depending on the requirements of the transducer 10.

In order to form the enclosed volume 3, the component 1 includes one or more surfaces 6 which extend between and are formed and/or joined to the contact surface 2 and the transducer surface 4, as shown in the cross-sectional view of FIG. 2. In the example, the one or more surfaces 6 are one surface which extends around the entire perimeter of the contact surface 2 and the transducer surface 4. In the example, the contact surface 2 and the transducer surface 4 are generally circular. One of the contact surface 2 and the transducer surface 4 can be larger in size than the other of the contact surface 2 and the transducer surface 4. In the example, the circular contact surface 2 is larger in diameter than the circular transducer surface 4. The enclosed volume 3 generally has the shape of a truncated cone, though other shapes can also be envisaged. In the example shown in FIGS. 1 and 2, the contact surface 2 forms the base surface of the truncated cone, and the one or more surfaces 6 form the tapering conical surface of the truncated cone. The angle between the one or more surfaces 6 and the contact surface 2 is greater than approximately 45 degrees but less than approximately 90 degrees. Though, less steep truncated cone shapes can also be envisaged. There is a radiused edge where the transducer surface 4 meets the one or more surfaces 6. Alternatively, the edge can be bevelled. As shown in FIG. 2, the boundary 7 enclosing the enclosed volume 3 comprises the contact surface 2, the transducer surface 4, and the one or more surfaces 6.

The flexible membrane and the boundary 7 around the enclosed volume 3 are fully formed by silicone, such that the entire enclosed volume 3 is defined fully by silicone. Though, other materials such as acrylic, nitrile, polyurethane or other elastomers can also be used.

Silicone is particularly advantageous in that it provides for good ultimate elongation, good tensile durability, high stretchability, and high flexibility, thus imparting flexibility and stretchability to the component 1. Additionally, silicone is washable, has excellent biocompatibility, excellent shelf life, is stable, is resistant to degradation, is chemically resistant, and implant quality grades are available. Silicone is therefore particularly advantageous in forming a component for use in a transducer arrangement which can be used to measure the vital signs of humans or animals. Furthermore, silicone is innately hydrophobic. This is advantageous for the purposes of self-cleaning, and also provides for benefits in the manufacturability of the component, which shall be discussed in the succeeding paragraphs. In addition, silicone is a material which mimics body tissue, and is a low-cost material.

Platinum-catalysed silicones can be used for forming the flexible membrane and/or the boundary 7. Platinum-catalysed silicones provide high quality in terms of surface finish, mechanical properties, elasticity, stretchability, softness, and conformability. Additionally, platinum-catalysed silicones also provide for improved chemical safety in terms of leachable substances, skin irritation, and ingestion safety. Examples of suitable platinum-catalysed silicones include Ecoflex 30 and Dragon Skin 10.

The liquid 8 which is contained within the enclosed volume 3 completely fills the enclosed volume, such that there is no air and/or any other fluid contained with the enclosed volume 3. The liquid 8 has a density substantially similar to the density of human or animal body tissue. This is advantageous because when used in a transducer arrangement 9 for measuring vital signs in the body of a human or animal, the liquid 8 can then provide for sound waves, for example, to travel through the body to the liquid 8 with minimal disruption to the wave propagation. This shall be discussed in more detail in the succeeding paragraphs.

The liquid 8 which is contained within the enclosed volume 3 provides flexibility and elasticity to the component 1. The liquid 8 has a low viscosity to impart improved flexibility and elasticity to the component 1. For example, the liquid can have a viscosity similar to that of water or oil or a gel. Optionally, the liquid 8 can have a low evaporation rate, to improve the stability of the properties and performance of the component 1 over time, and to ensure that the liquid 8 completely fills the enclosed volume 3 for as long as possible. For example, the liquid can have an evaporation rate similar to that of oil, which advantageously has a low evaporation rate, even with increasing temperature, to provide a stable component.

In the example, the liquid 8 is water. Though, other suitable liquids include, for example, oil or a gel such as PEG 400. Optionally, the water can be distilled water. Advantageously, this can reduce or avoid the inclusion of impurities and/or minerals in the liquid 8 to reduce or avoid the build-up of mineral deposits or other impurities in the enclosed volume 3 of the component 1 to ensure for stable properties and performance over time and to maintain the flexibility and stretchability of the component 1.

The component 1 might need to conform with and contact a curved, clothed and/or hairy surface. The combination of water encapsulated by silicone provides for good flexibility and elasticity of the overall component 1 to provide superior surface contact with a subject. Encapsulating water inside the boundary 7 imparts improved flexibility and elasticity to the boundary 7. Surprisingly, the component 1 is so flexible, stretchable and conformable that it can cover the curvature of the surface of a subject to close most air pockets in the surface, such as even those in between hairs or clothing. Additionally, providing improved surface contact facilitates the reduction of noise of a signal obtained using the component 1. Surprisingly, the reduction of noise is so high that an improved signal can be obtained even when using the component 1 on a hairy and/or clothed and/or moving subject such as the body of a human or animal. Further advantages of the combination of silicone and water shall be discussed in the succeeding paragraphs.

As illustrated in FIG. 3, a transducer arrangement 9 includes the component 1 and a transducer 10. As described earlier, the transducer surface 4 has a recess 5 which is configured to receive a transducer 10. The transducer 10 is mounted to or attached to and/or housed within the recess 5. Adhesive or other bonding means may be used. Alternatively, the transducer 10 can be though be mounted to or attached to the transducer 4 by another means.

In the example, the transducer 10 is a microphone. In this manner, the transducer arrangement 9 can be used to measure sound waves when the component 1 is placed on a subject such as the body of a human or animal, or a musical instrument. Though, the transducer 10 can be another sensor that is not a microphone. In this manner, the transducer arrangement 9 can adapted and used to measure any physical quantity when the component 1 is placed on a subject such as human or animal body, or a musical instrument.

In the example, the transducer is in the form of a microphone 10 such a commercially available microphone circuit (MAX9814) with a frequency response of 20 Hz-20 kHz. The transducer 10 is placed on top of the transducer surface 4 and enclosed by pouring and curing silicone, or any other flexible material, on top of it, to facilitate providing flexibility and stretchability to the transducer arrangement 9. The microphone has a built in automatic gain control with three levels, and distant sounds can be more amplified, improving the signal acquisition. Nearby "loud" sounds are quieted preventing signal clipping. The microphone amplifier is connected to a microcontroller (ESP32), which has a high processing power with an inbuilt analogue-to-digital converted (ADC). The sampling rate of the ADC can be set to 8 kHz. All recordings can be transmitted to a remote device via an inbuilt wi-fi module of the ESP32 microcontroller for the initiation, control and termination of the operation of the transducer arrangement 9. Besides remote transmission, an SD card module can also be used to store the data.

The operation and performance of the transducer arrangement 9 shall be discussed in more detail in the succeeding paragraphs.

Figure 4:
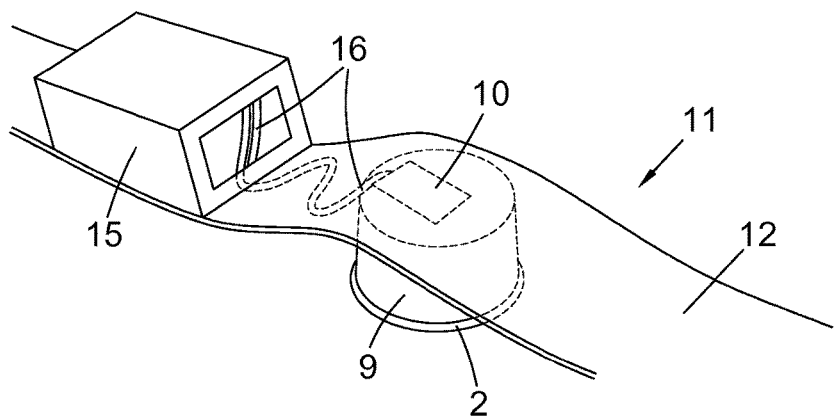
FIG. 4 illustrates a wearable transducer system.

As illustrated in FIG. 4, a wearable transducer system 11 includes the transducer arrangement 9 and a silicone strap 12 for attaching the transducer arrangement 9 to a human or animal subject. Alternatively, the strap 12 can be configured for attaching the transducer arrangement 9 to a non-human or non-animal object, such as a surface of a musical instrument.

The strap 12 includes a generally cuboidal volume 15 for receiving a printed circuit board (PCB). Wires 16 connecting the PCB to the transducer 10 are embedded inside the strap 12 to keep the wires 16 away from any environmental artefacts. Though, the wires 16 can be fixed to or attached to the strap 12 in any other way. A power source such as a battery can also be received by the volume 15.

Figures 5A, 5B:
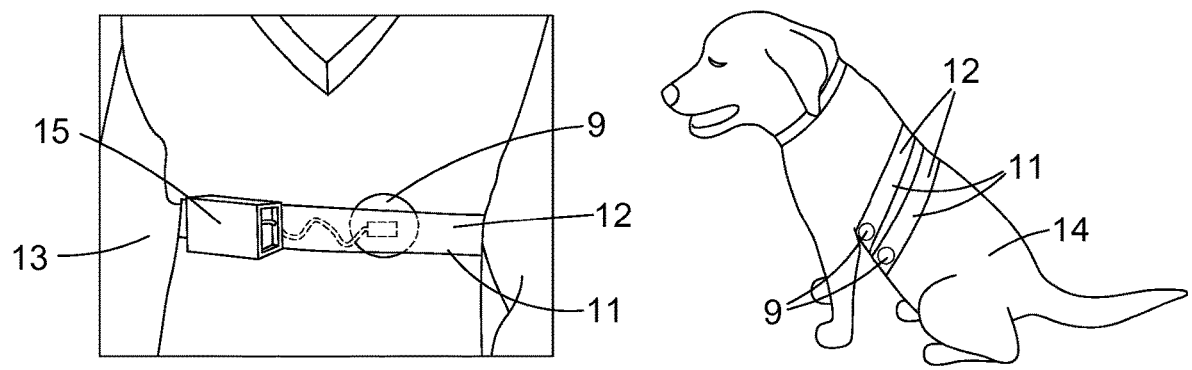
FIG. 5A illustrates a human subject wearing the wearable transducer system of FIG. 4.
FIG. 5B illustrates an animal subject wearing the wearable transducer system of FIG. 4.

FIGS. 5A and 5B show the wearable transducer system 11 being worn by a human subject 13 and an animal subject 14 respectively. The animal subject of FIG. 5B is wearing two wearable transducer systems 11.

The component 1, or the transducer arrangement 9, or the wearable transducer system 11 can be used to measure vital signs in humans or animals. The strap 12 can be used to place the wearable transducer system 11 on the body of a human or animal and hold it in place firmly. The resilient nature of the strap material can allow movement in the subject without undue loss of surface contact of the component 2. The transducer arrangement 9 can be used to measure a vital sign of a human animal body.

The transducer arrangement can provide for a means to record vital signs in humans or animals on moving bodies and/or on clothed and/or hairy surfaces. This is particularly advantageous because it means that skin does not need to be shaved and clothing does not need to be removed in order to measure vital signs. This is particularly advantageous in facilitating the continuous and unobtrusive monitoring of vital signs during daily routines. Furthermore, since the present disclosure provides for a means to record vital signs on clothed and/or hairy surfaces, due to improved conformity and contact, direct skin contact is not necessary. This is advantageous because it negates any possible skin irritation or allergic reactions.

In FIG. 5A, the wearable transducer system 11 is shown worn by a clothed human subject 13. In FIG. 5B, the wearable transducer system 11 is worn on an unshaved region of an animal subject. For an animal subject, vital signs can include, for example, heart rate, breathing rate, panting rate, and motion patterns. For a human subject, vital signs can include, for example, heart rate, breathing rate, and gut sounds. Measuring gut sounds can be used in the diagnosis of some digestive system diseases. It is also envisaged that the present disclosure can also be used to measure physical quantities such as sound waves from non-human and non-animal subjects, such as from a surface of a musical instrument. Though, the following discussion shall discuss the operation and performance of the present disclosure when used for measuring vital signs in humans or animals.

The performance of the component 1 (and hence associatively also the performance of the transducer arrangement 9 and the wearable transducer system 11, which include the component 1), which is formed of a silicone boundary 7 which defines an enclosed volume 3 which is filled with water 8, has been compared with two alternative devices: a component which comprises a silicone boundary filled with air, and a component which is solid silicone (i.e. with no cavity). The present disclosure and the two alternate devices will be referred to as the "water inside silicone device", the "air inside silicone device" and the "complete silicone device" respectively in the following description and associated figures. The performance of the water inside silicone device, the air inside silicone device and the complete silicone device were also compared with the performance of a known commercially available stethoscope diaphragm.

Figure 6:
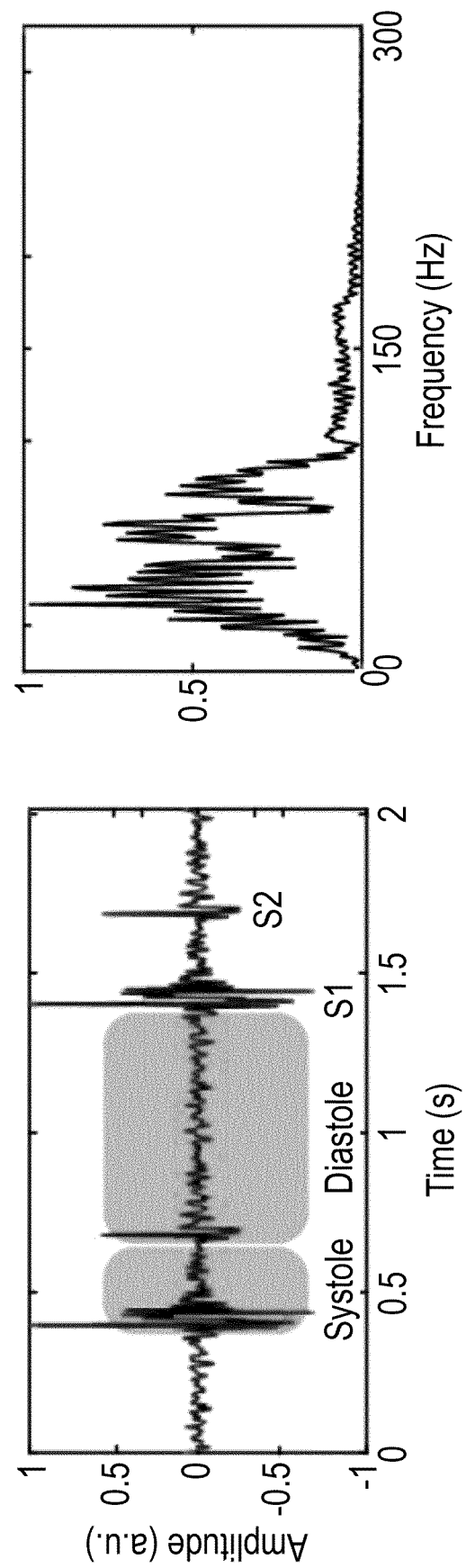
FIG. 6 shows the time and frequency domain graphics of normal heart sound signals.

As a reference, a normal heart sound signal with a rhythm of 60 beats per minute recorded by a digital stethoscope was used. The signal was obtained from ThinkLabs Medical LLC. The normal heart sound was played using a cylindrical speaker, and the transducer arrangement 9, was placed on top of the speaker. FIG. 6 depicts the time and frequency domain graphics of normal heart sound signals and demonstrates that heart sounds are most observable in the frequency range of 20-150 Hz. In comparing the three devices and the stethoscope diaphragm, constant audio volume and environmental conditions were employed.

FIG. 7A shows the raw heart sound signals which were recorded using the four devices: the stethoscope diaphragm, the water inside silicone device, the air inside silicone device, and the complete silicone device. FIG. 7B shows the same four heart sound signals filtered. The other three devices tested were sized to have the same size of the depth d1 as the water inside silicone device, which has a value of d1 of approximately 15 mm.

FIG. 7A shows that the signal recorded with the stethoscope diaphragm is less noisy than the complete silicone transducer but noisier than the signals collected with the water inside silicone and air inside silicone devices. FIG. 7A thus shows that sound waves are attenuated most in the air inside silicone device, compared with the water inside silicone device and the complete silicone device. In particular, the signal recorded with the air inside silicone device exhibits high attenuation of heart sounds which causes difficulty in the recognition of S1 and S2 heart sounds. FIG. 7A shows that in the signal recorded by the complete silicone transducer, over-amplification of the heart sounds results in signal clipping especially in the S1 and S2 heart sound regions. As such, in the signal recorded by the complete silicone transducer, there is a loss of critical information. Such information loss could be reduced by reducing the amplification, however this would disadvantageously reduce the sensitivity of the sound recording. Furthermore, the complete silicone transducer does not conform to a subject such as the body of a human or animal well, and the motion of air particles in the area between the transducer and the surface of the subject being measured, such as on a hairy or clothed surface, results in an increase in the amount of noise in the signal recording.

As shown in FIG. 7A by the signal for the water inside silicone device, it was surprisingly found that providing a component 1 which includes a silicone boundary 7 encapsulating an enclosed volume 3 filled with water 8 makes the component 1 softer and more flexible and elastic, and provides for improved contact with the surface of a subject. Furthermore, signals such as sound waves are less attenuated in water than in air or in solid silicone. As shown in FIG. 7A, this results in the observation of the S1 and S2 heart sounds clearly without any clippings for the water inside silicone device. As such, the water inside silicone device shows the best performance compared with the stethoscope diaphragm, the air inside silicone device, and the complete silicone device.

The filtered signals of FIG. 7A are shown in FIG. 7B. The raw signals were normalised between −1 and 1 and a bandpass filter (infinite impulse response (IIR) Chebyshev filter) was applied, allowing frequencies between 20-150 Hz to pass. In the filtered signals, the amplitude of the recorded signal with the air inside silicone device exhibits an increase such that the S1 and S2 heart sounds become more distinguishable compared with the raw signals for the air inside silicone device. On the other hand, the filtered signal from the complete silicone device is very noisy such that the S1 and D2 heart sounds are not easily distinguishable, even after band pass filtering. The sound quality in the case of the water inside silicone device improves after the filtering, and as shown by comparing FIGS. 7A and 7B, in the case of the water inside silicone device, the shape of the filtered signal resembles closely the original raw signal. For the water inside silicone device, the raw signal acquired is very similar to the signal after filtering. This is highly advantageous because the component 1 is thus able to act as a natural band-pass filter in the acquisition of signals, such as for example, heart sounds.

In optimising the performance of the transducer, it has been shown that when applying the same band pass filter as that used on the signals of FIG. 7B, in order to obtain the best quality of signal, the optimum value for the first depth d1 of the liquid 8 contained within the enclosed volume 3 is approximately 15 mm.

Figure 8A:
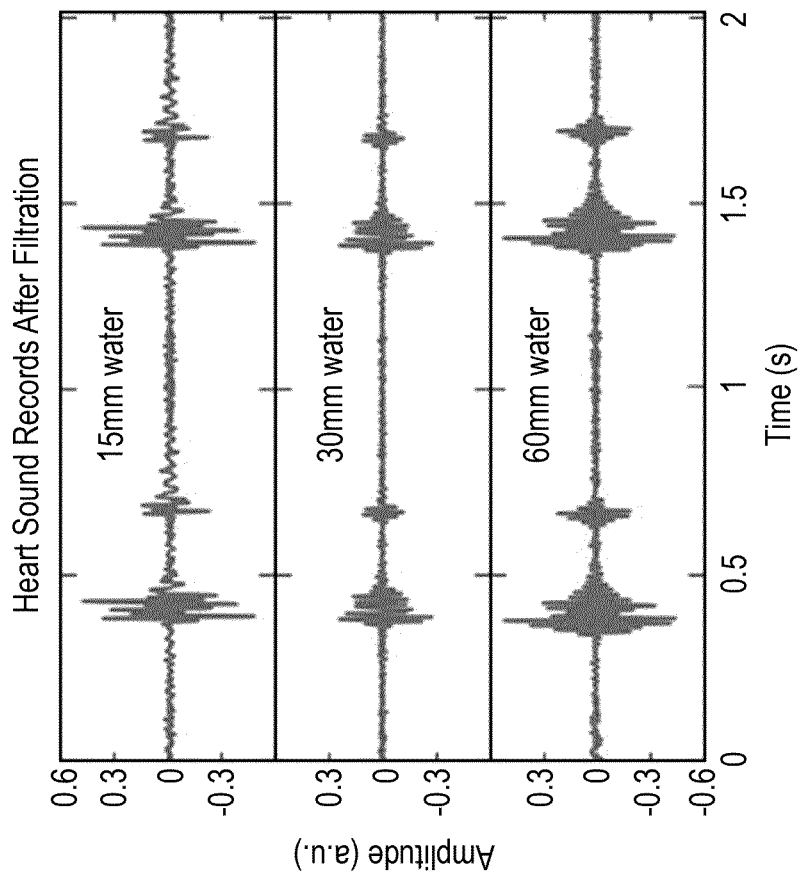
FIG. 8A shows raw heart sound signals collected using three different exemplary transducer arrangements.
Figure 8B:
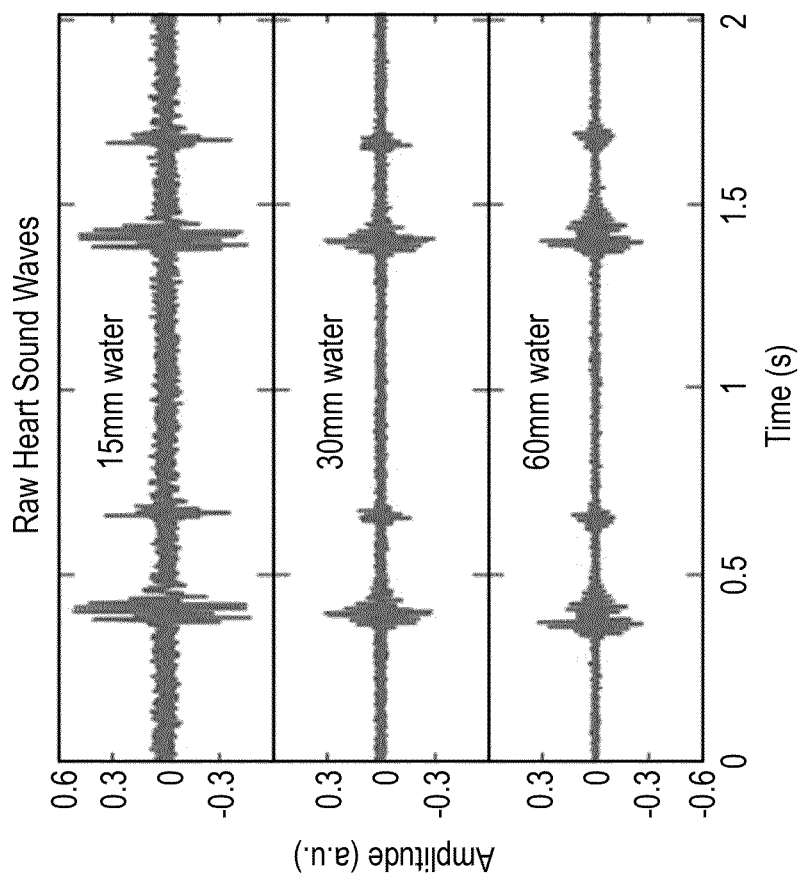
FIG. 8B shows the heart sound signals of FIG. 7B filtered.

FIG. 8A shows a comparison of the raw heart sound signals obtained using water inside silicone devices including components 1 with values of d1 of approximately 15 mm, approximately 30 mm and approximately 60 mm respectively. FIG. 8B shows the heart sounds of FIG. 8A filtered by applying the same band pass filter as that described above in relation to FIG. 7B. FIG. 8A shows that as d1 increases, the raw heart sound signals are more attenuated, but less noisy. As such, by balancing the effects of increasing attenuation and reduced noise and by also taking into account the stiffnesses of the silicone and water, FIGS. 8A and 8B show that the best quality of signal is obtained when d1 is approximately 15 mm.

FIG. 9 shows a comparison of two components 1 whose boundaries 7 are formed of two different exemplary platinum-catalysed silicones-Ecoflex 30 and Dragon Skin 10 respectively. The performance of Ecoflex 30 and Dragon Skin 10 were compared to see how elasticity and hardness of the boundary 7 affects the operation of the component 1 and the transducer arrangement 9. Ecoflex 30 is softer and more elastic than Dragon Skin 10.

Dynamic time warping (DTW) is a robust distance measure to compare non-linear time series in different speeds without any effects of consecutive repetition and provides a time invariant method to compare audio signals. The DTW algorithm was used to measure the similarity between the recorded heart sounds and the played heart sounds. To bring all the signals to the same reference, the recordings were normalised from −1 to 1 to reduce the sound attenuation. The normalised signals were then filtered between 20-150 Hz. The DTW algorithm was then applied, and the resulting signals were then normalised between 0 to 1. The resulting data is shown in FIG. 9. The numbers in the table of FIG. 9 represent the scores calculated using the DTW algorithm.

The drawback of this comparison method is that the noise of the signals with low amplitudes (e.g. the air with silicone device with a d1 value of 15 mm) is amplified much more than the noise of the signals with higher amplitudes (e.g. the complete silicone device with a d1 value of 15 mm), resulting in low similarity indices respectfully.

FIG. 9 shows that all the devices encapsulated with a boundary formed of Ecoflex 30 silicone outperformed all the devices encapsulated with a boundary formed of Dragon Skin 10, except for the device with a d1 value of 30 mm encapsulated with a boundary formed of Dragon Skin 10. FIG. 9 shows that most of the devices encapsulated with a boundary formed of silicone performed better than the diaphragm of a commercial stethoscope. Among all the devices tested, the water inside silicone device with a boundary 7 formed of Ecoflex 30 and a d1 value of 30 mm showed the best performance. However, larger values of d1 will cause more movement of a component 1 and a transducer 10 on a body. As such, preferably, the boundary 7 is formed of Ecoflex 30 platinum-catalysed silicone, and d1 has a value of approximately 15 mm.

According to the exemplary setup of FIG. 5A, in which the wearable transducer system 11 was attached to a human subject 13, it has been shown that the component 1 provides for the unobtrusive acquisition of vital signs without the need to shave the skin, use conductive gel, or remove clothing. FIG. 10A shows the raw heart sounds recorded using the component 1, in which the boundary 7 is preferably formed of silicone and the liquid is preferably water, of a clothed human subject, compared with those measured using a known commercially available stethoscope diaphragm. FIG. 10B shows the raw heart sound signals of FIG. 10A normalised and filtered using Butterworth band pass filter in a frequency range of 20-150 Hz.

As shown in FIG. 10A, since the stethoscope diaphragm is solid and does not conform to the subject (for example, a human body) very well, the amplitude of the recorded signal is very low, and the heart sounds S1 and S2 are very difficult to detect without any amplification.

Furthermore, even though the S1 heart sounds are recovered after bandpass filtering in a frequency range of 20-150 Hz, the S2 sounds are still not visible in the signal measured using the stethoscope diaphragm. On the other hand, as shown clearly in FIGS. 10A and 10B, both the S1 and S2 heart sounds can be detected using the water inside silicone device. The heart sounds have much higher amplitudes, because the water inside silicone device of the present disclosure is flexible and establishes better contact than the known stethoscope diaphragm by conforming to the shape of the body surface. Moreover, the clear visibility of heart sounds and low background noise even before filtering, as shown in FIG. 10A, demonstrates that the water inside silicone device can eliminate any environmental artefacts significantly. As previously described in relation to FIGS. 7A and 7B, a further advantage is that there is little difference between the signal obtained using the water inside silicone device before and after filtering, indicating that the water inside silicone device behaves like a band-pass filter, thus increasing the usability and usefulness of the raw signal obtained.

According to the exemplary setup of FIG. 5B, in which two wearable transducer systems 11 were attached to an animal subject 14, a Labrador Retriever, it has been shown that the component 1 can provide for the unobtrusive acquisition of vital signs in animals, despite hairy skin and animal movement. Two identical wearable transducer systems 11 can be used simultaneously for the sake of data reliability, since the signal recording may be disturbed if one of the animal's legs touches the transducer arrangement 9 during walking and sitting.

When measuring vital signs in animals, besides environmental artefacts, heart sounds can also be obscured by internal artefacts such as heavy breathing and/or panting of the animal 14. For example, the intense and frequent panting of a Labrador Retriever can cause serious signal clippings such that proper heart sound recording may not be achievable. In addition, the motion of the animal 14 may cause the transducer arrangement 11 to move back and forth, resulting in improper sound recordings.

FIG. 11A shows heart sound signals recorded using the component 1 when the animal 14 is sitting and not panting. Due to the aforementioned artefacts, there is still much noise during the diastole phase of the heart. Though, this noise can be eliminated using the noise reduction algorithm of the Audacity program, for example. FIG. 11B shows the signal of FIG. 11A after noise reduction and band pass filtering with a frequency of 15-100 Hz. The frequency of breathing and heart sounds and murmurs are different from each other and the breathing sound and murmurs can be eliminated from the heart sound using noise reduction algorithms, as shown in FIG. 11B. As highlighted in FIG. 11A, the breathing sound in the recorded animal heart sound signal occurs in the middle of two heart sounds, one S2 and one S1, which corresponds to the diastole phase of the heart cycle. This region was labelled as a noise profile and using the Audacity program, a noise reduction algorithm was applied. The highest frequencies of breathing sounds were observed between 447 and 1323 Hz for inspiration, and between 206 and 540 Hz for expiration. A band pass filter of 15-100 Hz was therefore used to improve the observation of heart sounds by eliminating environmental noise including breathing sounds. The resulting signal shows both S1 and S2 regions, with the breathing data mostly clearly eliminated.

The recording of heart sounds in animals such as dogs can be improved by forming a strap 12 of a harder elastomer, such as a harder silicone such as Dragon Skin 10. This is because a harder elastomer will wrap the animal's body more snugly and keep the transducer arrangement 9 tightly in position, regardless of any motion of the animal 14.

The wearable transducer system 11 can further comprise an additional transducer such as, for example, an elastomeric strain sensor. This additional sensor can be used to measure the change in chest position of a human or animal subject. For an animal subject, this additional sensor can be used to detect the rate and frequency of breathing and/or panting. Heart sounds recorded using the wearable transducer system 11 could then be obtained by filtering out the panting and breathing data obtained using the additional sensor. Moreover, audio and acceleration records of the chest can also improve the identification of heart sounds, breathing rates and panting rates.

When used for measuring vital signs in animals, the transducer 10 can be a digital MEMS microphone that eliminates electronic noise. Advantageously, this will improve the quality of a sound signal recorded from an animal subject.

Advantageously, the present disclosure provides a means to measure vital signs in humans and animals without the need for conductive gels, shaving of the skin, or removal of clothing, and regardless of a subject's chest moving back and forth due to intense breathing. It has been shown that the component 1 performs well in reducing significant noise or loss of important information during the measuring of vital signs in humans or animals. The component 1, the transducer arrangement 9, and the wearable transducer system 11 are thus advantageously suitable to be used for remote and unobtrusive monitoring of vital signs in humans and animals. Undesired frequencies can be filtered out using digital filters to further improve the sensitivity and stability of recordings obtained using the component 1.

Although the foregoing description of the operation and performance of the component 1, the transducer arrangement 9 and the wearable transducer system 11 has made reference to measuring vital signs in human or animal subjects, the component 1, the transducer arrangement 9, and the wearable transducer system 11 can be used to measure any physical quantity from any subject or object. For example, a subject can be the body of a human or animal, such as a human or a dog or other pet. As another example, a subject/object can be a musical instrument, such as a guitar or violin or other string instrument, or a brass instrument such as a trumpet or trombone. Musical instruments can include surfaces having complex curvatures. The component 1 is flexible and stretchable and is able to conform well to a range of surfaces, making it useful for recording sounds from musical instruments despite their complex morphology, and for conforming to the surfaces of human or animal bodies, even if they are clothed and/or hairy.

Figure 12A:
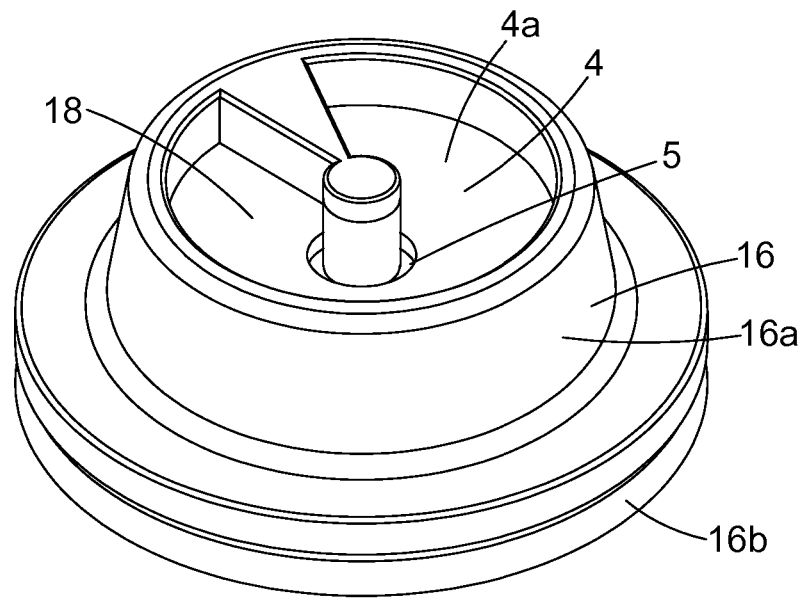
FIG. 12A illustrates a mould arrangement which may be used in a method for manufacturing a component.
Figure 12B:
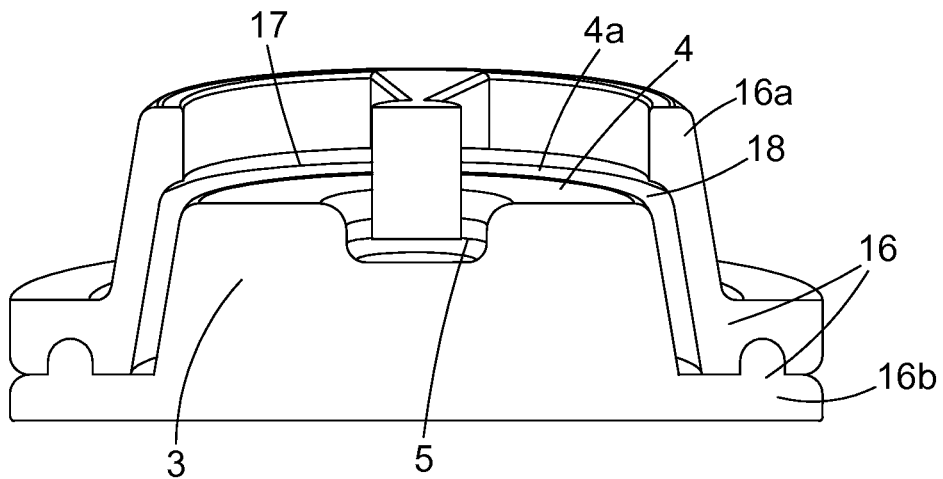
FIG. 12B illustrates a cross-sectional view of the mould arrangement of FIG. 12A.

FIGS. 12A and 12B show a mould arrangement 16 which can be used in a method of manufacturing the component 1. The mould arrangement 16 is fabricated using an additive manufacturing process such as 3D printing. The mould arrangement 16 defines a shape which defines at least partially the enclosed volume 3. The mould arrangement 16 has a first portion 16*a* and a second portion 16*b*. Between the first and second portions 16*a*, 16*b* of the mould arrangement 16, there is at least partially defined a cavity 17 which defines a three-dimensional volume which is at least partially concave and at least partially hollow and which at least partially defines the enclosed volume 3.

In another step of the method, a first portion 18 of pre-polymer elastomer, for example liquid silicone, is poured or introduced into the mould arrangement 16. In the example, the first portion of pre-polymer elastomer comprises liquid silicone, though it is envisaged that any other suitable pre-polymer elastomer may be used. The first portion 18 of liquid silicone is then at least partially cured to form a first silicone portion which defines at least partially the enclosed volume 3. The first portion 18 of liquid silicone can be at least partially cured at room temperature. Typically, the first portion 18 of liquid silicone can take approximately two hours to become solid but not fully cured, and can take weeks to fully cure. The first silicone portion comprises the transducer surface 4, the recess 5, and the one or more surfaces 6. Alternatively, it is envisaged that the first silicone portion can comprise the contact surface 2 and the one or more surfaces 6.

Figure 13:
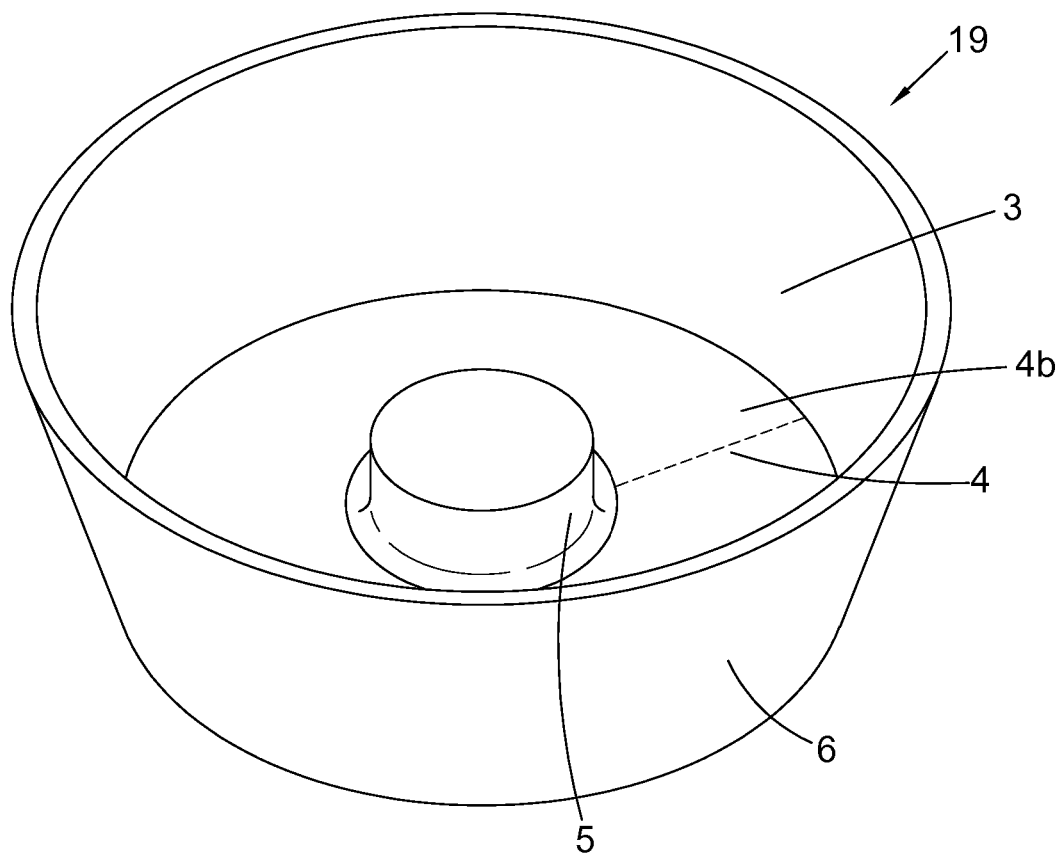
FIG. 13 illustrates a silicone portion formed using the mould of FIG. 12A.

The first silicone portion is then removed from the mould arrangement 16. A mould release agent can be applied to the surfaces of the mould arrangement 16 before the first portion 18 of silicone is poured into the mould arrangement 16, in order to ease the removal of the at least partially cured first silicone portion. FIG. 13 shows an exemplary first silicone portion 19. A liquid 8 is then poured or introduced into the partially enclosed volume 3 defined by the first silicone portion to fully fill the partially enclosed volume 3 with liquid 8. In the example, the liquid 8 comprises water, though it is envisaged that any other suitable liquid may be used, such as, for example, one or more of water or oil or a gel. It should be understood that the first silicone portion can be orientated in an opposite vertical orientation from that shown in FIGS. 12A and 12B in order to facilitate the filling of the partially enclosed volume 3 with water. FIG. 13 shows the vertical orientation which facilitates the filling of the partially enclosed volume 3 with water.

Then, a second portion of pre-polymer elastomer, for example liquid silicone, is poured or introduced on top of the water. In the example, the second portion of pre-polymer elastomer comprises liquid silicone, though it is envisaged that any other suitable pre-polymer elastomer may be used. Advantageously, since silicone is very hydrophobic in its pre-polymer (i.e. uncured) state, the second portion of liquid silicone will not mix with the water 8 or sink. As such, the second portion of liquid silicone will form a film on top of the water 8. This is advantageous because it prevents the formation of air bubbles in the enclosed volume 3. Furthermore, the second portion of liquid silicone will stick to and cure together with the at least partially cured first portion 18 of liquid silicone, to form a monolithic boundary 7.

The second portion of liquid silicone is then at least partially cured to form a substantially planar second silicone portion on top of the water 8. The second portion of liquid silicone can be at least partially cured at room temperature. Typically, the second portion of liquid silicone can take approximately two hours to become solid but not fully cured, and can take weeks to fully cure. The second silicone portion can comprise the contact surface 2. Alternatively, it is envisaged that the second silicone portion can comprise the transducer surface 4.

The first silicone portion and the second silicone portion have a generally constant material thickness of approximately 2 mm. Before they are poured into the mould arrangement 16 and on top of the water 8 respectively, the first portion 18 of liquid silicone and the second portion of liquid silicone can be placed on a vacuum chamber for degassing until some or all bubbles are removed. The first portion 18 of liquid silicone can be degassed again to remove any remaining bubbles after it has been poured into the mould arrangement 16.

The first and second pre-polymer elastomer portions and the liquid may be any materials which provide that the liquid maintains the second portion of pre-polymer elastomer on top of said liquid through surface tension or density and does not prevent the curing, polymerisation and/or cross-linking of the second portion of pre-polymer elastomer to form the second elastomer portion. Advantageously, the second portion of pre-polymer elastomer will not mix with the liquid or sink. Advantageously, this prevents the formation of air bubbles in the enclosed volume and the second portion of pre-polymer elastomer will stick to and cure together with the at least partially cured first portion of pre-polymer elastomer. The transducer arrangement 9 can be manufactured according to the foregoing method. The recess 5 can be provided on one or more of the first or second silicone portions. The transducer 10 can be mounted or attached to and/or housed within the recess 5. The transducer 10 can be a sensor such as an audio sensor, for example, a microphone. The sensor can optionally be encased with a flexible material such as silicone, in order to improve the flexibility of the transducer arrangement 9. Furthermore, since silicone is a non-conductive material, it separates the sensor from the external surroundings. Encasing the sensor with silicone can therefore improve the quality of the signals obtained using the sensor, by significantly attenuating environmental artefacts.

It is envisaged that the foregoing method for manufacturing the component 1 need not employ silicone and water.

For example, oil or a gel such as PEG 400 can be used in place of water. For example, any flexible material such as an elastomer comprising one or more of silicone, acrylic, nitrile and polyurethane can be used in place of silicone. Though, it has been noted that the optimum combination of materials is silicone and water. This combination provides good flexibility and good conformity to the surface of a subject, such as the body of a human or animal or a musical instrument. Furthermore, since silicone is hydrophobic in its pre-polymer state, the second silicone portion is able to be poured onto the water without mixing with the water inside the enclosed volume 3, and stick to and/or cure with the first silicone portion. This prevents the formation of air bubbles and provides improved manufacturability to the component 1. Other elastomers can require modifications during synthesis to make them hydrophobic.

The component 1 and associated methods described herein have a number of advantages. The component 1 is relatively low in cost compared to a commercial electronic stethoscope. It has been shown that the transducer arrangement 9 can be used as an unobtrusive measurement device to continuously monitor vital signs of humans or animals during daily routines. The unique combination of silicone and water provides for an improved manufacturing process, with liquid silicone staying and curing on top of the surface of the water and sticking to previously partially cured silicone to form a uniform part. The component 1 is also flexible and stretchable and able to conform to surfaces well with good contact, and surprisingly, even to hairy, clothed or curved surfaces. This provides for reduced skin irritation and allergic reactions when used on skin, and improved signal recording. Furthermore, surprisingly, the component 1 is able to act as a natural band-pass filter in the acquisition of signals, such as for example, heart sounds. In measuring heart sounds, advantageously the component 1 is able to detect both the S1 and S2 heart sounds. Additionally, silicone mimics body tissue, and when used in combination with water, the component 2 can thus provide for sound waves, for example, to travel through the body to the liquid 8 with minimal disruption to the wave propagation, thus providing an improved signal recording. The component and associated methods described herein can be advantageous not only for measuring vital signs or other signals from humans or animals, but also for measuring physical quantities such as sound waves from other subjects such as musical instruments or other sound-producing devices.

The invention claimed is:

1. A component for use in a transducer arrangement, the component comprising:
   a flexible membrane defining a contact surface, wherein the flexible membrane further at least partially defines an enclosed volume;
   a liquid contained within the enclosed volume; and
   a surface configured to receive a transducer,
   wherein the contact surface and the surface configured to receive a transducer are substantially parallel; and
   wherein the surface configured to receive a transducer defines an external recess configured to receive the transducer.

2. A component as claimed in claim 1, wherein the flexible membrane comprises an elastomer.

3. The component of claim 1, wherein the enclosed volume is defined fully by an elastomer.

4. The component of claim 2 wherein the elastomer comprises one or more of silicone, acrylic, nitrile and polyurethane.

5. The component of claim 1, wherein at least a part of a boundary enclosing the enclosed volume has a material thickness of between approximately 0.05 mm to approximately 5 mm.

6. The component of claim 1, wherein the contact surface is substantially planar.

7. The component of claim 1, wherein the contact surface is generally circular or elliptical in shape.

8. The component of claim 1, wherein a maximum internal spacing in a direction substantially perpendicular to the contact surface between the contact surface and the surface configured to receive a transducer defines a first depth of the liquid; wherein the first depth of the liquid is between approximately 5 mm to approximately 70 mm.

9. The component of claim 1, wherein the internal spacing in a direction substantially perpendicular to the contact surface between the contact surface and the surface configured to receive a transducer in the region of the recess defines a second depth of the liquid; wherein the second depth of the liquid is between approximately 1 mm to approximately 10 mm less than the first depth.

10. The component of claim 1, wherein the component further comprises one or more additional surfaces extending between the contact surface and the surface configured to receive a transducer, such that the enclosed volume is defined fully therebetween.

11. The component of claim 10, wherein the enclosed volume generally has the shape of a truncated cone.

12. The component of claim 1, wherein the liquid has a density substantially similar to a density of a human or animal body tissue.

13. The component of claim 12, wherein the liquid comprises one or more of water and oil and a gel.

14. The component of claim 1, wherein the liquid completely fills the enclosed volume.

15. A transducer arrangement comprising the component of claim 1, and a transducer.

16. The transducer arrangement of claim 15, wherein the transducer is configured to measure sound.

17. The transducer arrangement of claim 16, wherein the transducer is an electret microphone.

18. A wearable transducer system comprising the transducer arrangement of claim 15, and an attachment element for attaching the transducer arrangement to a human or animal.

19. The wearable transducer of claim 18, wherein the attachment element comprises an elastomer.

20. A method of measuring vital signs in humans or animals using the component of claim 1.

21. A method for manufacturing a component, the method comprising:
   providing a mould arrangement defining a shape which defines a partially enclosed volume;
   introducing a first portion of pre-polymer elastomer into the mould arrangement;
   at least partially curing the first portion of pre-polymer elastomer to form a first elastomer portion which defines a partially enclosed volume;
   introducing a liquid into the partially enclosed volume defined by the first elastomer portion to fully fill the partially enclosed volume;
   introducing a second portion of pre-polymer elastomer on top of the liquid; and
   at least partially curing the second portion of pre-polymer elastomer to form a substantially planar second elastomer portion on top of the liquid.

22. The method for manufacturing the component of claim 21, further comprising:
   providing a recess in one of the first or second elastomer portions; and
   mounting a transducer in the recess.

\* \* \* \* \*